United States Patent
Le et al.

(10) Patent No.: US 7,620,444 B2
(45) Date of Patent: Nov. 17, 2009

(54) SYSTEMS AND METHODS FOR IMPROVING USABILITY OF IMAGES FOR MEDICAL APPLICATIONS

(75) Inventors: Toan Thanh Le, Germantown, WI (US); Shiying Hu, Waukesha, WI (US); Kishore Chandra Acharya, Brookfield, WI (US); David A. Caumartin, Saint Cloud (FR); Karen Ann Procknow, Willowbrook, IL (US)

(73) Assignee: General Electric Company, Schenectady, NY (US)

( * ) Notice: Subject to any disclaimer, the term of this patent is extended or adjusted under 35 U.S.C. 154(b) by 411 days.

(21) Appl. No.: 10/678,839

(22) Filed: Oct. 3, 2003

(65) Prior Publication Data
US 2004/0138557 A1 Jul. 15, 2004

Related U.S. Application Data

(60) Provisional application No. 60/415,992, filed on Oct. 5, 2002.

(51) Int. Cl.
*A61B 5/05* (2006.01)
(52) U.S. Cl. .......................... 600/428; 600/425; 378/8; 378/4; 378/15
(58) Field of Classification Search .................. 600/428, 600/425; 378/8, 4, 15
See application file for complete search history.

(56) References Cited

U.S. PATENT DOCUMENTS

| | | | |
|---|---|---|---|
| 3,861,807 A | 1/1975 | Lascrenler | |
| 3,871,360 A | 3/1975 | Van Horn et al. | |
| 3,952,201 A | 4/1976 | Hounsfield | |
| 4,031,884 A | 6/1977 | Henzel | |
| 4,262,306 A | 4/1981 | Renner | |
| 4,463,425 A | 7/1984 | Hirano et al. | |
| 4,994,965 A | 2/1991 | Crawford et al. | |
| 5,080,100 A | 1/1992 | Trotel | |
| 5,271,055 A | 12/1993 | Hsieh et al. | |
| 5,279,309 A | 1/1994 | Taylor et al. | |
| 5,295,483 A | 3/1994 | Nowacki et al. | |
| 5,315,630 A | 5/1994 | Sturm et al. | |

(Continued)

FOREIGN PATENT DOCUMENTS

DE 43 41 324 A 1 6/1995

(Continued)

OTHER PUBLICATIONS

Mostafavi, Hassan; "Overview of Post-Processing Algorithm to Create Volumetric Motion Sequences"; Varian Medical Systems, Inc.; May 2, 2002.*

(Continued)

*Primary Examiner*—Brian Casler
*Assistant Examiner*—John F Ramirez
(74) *Attorney, Agent, or Firm*—Armstrong Teasdale LLP

(57) ABSTRACT

A method for retrospective internal gating is provided. The method includes scanning a patient to obtain projection data, generating images from the projection data, generating a signal representing information regarding a physiological cycle of an object within the patient, specifying at least one target phase based on which the images can be sorted, and sorting the images based on the target phase within a cycle of motion of the object to generate at least one series of images.

21 Claims, 10 Drawing Sheets

U.S. PATENT DOCUMENTS

| | | | |
|---|---|---|---|
| 5,389,101 | A | 2/1995 | Heilbrun et al. |
| 5,394,875 | A | 3/1995 | Lewis et al. |
| 5,446,548 | A | 8/1995 | Gerig et al. |
| 5,538,494 | A | 7/1996 | Matsuda |
| 5,582,182 | A | 12/1996 | Hillsman |
| 5,603,318 | A | 2/1997 | Heilbrun et al. |
| 5,727,554 | A | 3/1998 | Kalend et al. |
| 5,764,723 | A | 6/1998 | Weinberger et al. |
| 5,784,431 | A | 7/1998 | Kalend et al. |
| 5,823,192 | A | 10/1998 | Kalend et al. |
| 5,836,954 | A | 11/1998 | Heilbrun et al. |
| 5,954,647 | A | 9/1999 | Bova et al. |
| 6,138,302 | A | 10/2000 | Sashin et al. |
| 6,146,390 | A | 11/2000 | Heilbrun et al. |
| 6,165,181 | A | 12/2000 | Heilbrun et al. |
| 6,185,445 | B1 | 2/2001 | Knüttel |
| 6,185,446 | B1 | 2/2001 | Carlsen, Jr. |
| 6,198,959 | B1 | 3/2001 | Wang |
| 6,370,217 | B1 | 4/2002 | Hu et al. |
| 6,526,117 | B1 * | 2/2003 | Okerlund et al. ............... 378/8 |
| 6,621,889 | B1 | 9/2003 | Mostafavi |
| 7,006,862 | B2 * | 2/2006 | Kaufman et al. ............ 600/523 |
| 2002/0023652 | A1 | 2/2002 | Riaziat et al. |
| 2003/0007593 | A1 * | 1/2003 | Heuscher et al. ............... 378/4 |
| 2003/0063292 | A1 | 4/2003 | Mostafavi |
| 2003/0072419 | A1 | 4/2003 | Bruder et al. |

FOREIGN PATENT DOCUMENTS

| | | |
|---|---|---|
| FI | 79458 | 9/1989 |
| WO | WO 98/16151 | 4/1998 |

OTHER PUBLICATIONS

Peltola, Seppo M.Sc.; "Gated Radiotherapy To Compensate For Patient Breathing"; *Proceedings of the Eleventh Varian Users Meeting*; Macro Island, Florida; May 11-13, 1986.

Mah, Katherine, et al.; "Time Varying Does Due To Respiratory Motion During Radiation Therapy Of The Thorax"; *Proceedings of the Eighth Int'l Conference on the Use of Computers In Radiation Therapy*, Toronto, Canada; Jul. 9-12, 1984; pp. 294-298.

Mori, Masayuki, et al.; "Accurate Contiguous Sections Without Breath-Holding On Chest CT: Value of Respiratory Gating and Ultrafast CT"; *AJR:162*, May 1994; pp. 1057-1062.

Robinson, Terry E., et al.; "Standardized High-Resolution CT of the Lung Using A Spirometer-Triggered Electron Beam CT Scanner"; *AJR:172*; Jun. 1999; pp. 1636-1638.

Luker, Gary D., et al.; "Ghosting of Pulmonary Nodules With Respiratory Motion: Comparison of Helical and Conventional CT Using an In Vitro Pediatric Model"; *AJR:167*; Nov. 1996; pp. 1189-1193.

Li, Debiao. et al.; "Coronary Arteries: Three-dimensional MR Imaging With Retrospective Respiratory Gating"; *Radiology*; Dec. 1996; vol. 201; No. 3.; pp. 857-863.

Kachelriess, Marc, et al.; "Electrocardiogram-correlated Image Reconstruction From Subsecond Spiral Computed Tomography Scans Of The Heart"; *Med. Phys. 25*(12); Dec. 1998; pp. 2417-2431.

Tada, Takuhito, et al.; "Lung Cancer; Intermittent Irradiation Synchronized With Respiratory Motion-Results Of A Pilot Study"; *Radiology*, Jun. 1998; vol. 207; No. 3; pp. 779-783.

Solberg, Timothy D., et al.; "Feasibility of Gated IMRT"; 3 pps.

Wong, John W., et al.; "The Use Of Active Breathing Control (ABC) To Reduce Margin For Breathing Motion"; *Int. J. Radiation Oncology Biol. Phys.*; 1999; vol. 44; No. 4; pp. 911-919.

Mageras, Gig, et al.; "Initial Clinical Evaluation Of A Respiratory Gating Radiotherapy System"; *Dept. of Medical Physics. Memorial Sloan-Kettering Cancer Center*, New York; 4 pps.

Yorke, Ellen, et al.; "Respiratory Gating Of Sliding Window IMRT"; *Dept. of Medical Physics, Memorial Sloan-Kettering Cancer Center*, New York; 4 pps.

Keatley, Eric, et al.; "Computer Automated Diaphragm Motion Quantification in a Fluoroscopic Movie"; *Dept. of Medical Physics, Memorial Sloan-Kettering Cancer Center*, New York; 3 pps.

Kubo, H. Dale, et al.; "Breathing-Synchronized Radiotherapy Program at the University of California Davis Cancer Center"; *Med. Phys. 27*(2); Feb. 2000; pp. 346-353.

Iwasawa, Tae, et al.; "Normal In-Plane Respiratory Motion of the Bilateral Hemidiaphragms Evaluated By Sequentially Subtracted Fast Magnetic Resonance Images"; *Journal of Thoracic Imaging*; 1999; vol. 14, No. 2; pp. 130-134.

Kim, W.S., et al.; "Extension of Cardiac and Respiratory Motion Cycles by Use of Projection Data and Its Applications to NMR Imaging"; *Magnetic Resonance in Medicine* 13; 1990; pp. 25-37.

Woodard, Pamela K., et al.; "Detection of Coronary Stenoses on Source and Projection Images Using Three-Dimensional MR Angiography With Retrospective Respiratory Gating: Preliminary Experience"; *AJR:170*; Apr. 1998; No. 4; pp. 883-888.

Sinkus, Ralph, et al.; "Motion Pattern Adapted Real-Time Respiratory Gating"; *Magnetic Resonance in Medicine 41*; 1999; pp. 148-155.

Weiger, Markus, et al.; "Motion-Adapted Gating Based on k-Space Weighting For Reduction of Respiratory Motion Artifacts"; *Magnetic Resonance in Medicine* 38; 1997; pp. 322-333.

Wang, Yi, et al.; "Implications For The Spatial Resolution in Coronary Imaging"; *Magnetic Resonance in Medicine* 33: 1995; pp. 713-719.

Ritchie, Cameron J., et al.; "Predictive Respiratory Gating: A New Method To Reduce Motion Artifacts on CT Scans"; *Radiology*; 1994; pp. 847-852; vol. 190: No. 3.

Kubo, H. Dale, et al.; "Potential and Role of a Prototype Amorphous Silicon Array Electronic Portal Imaging Device in Breathing Synchronized Radiotherapy"; *Med. Phys. 26*(*11*); Nov. 1999; pp. 2410-2414.

Kubo, Hideo D., et al.; "Respiration Gated Radiotherapy Treatment: A Technical Study"; *Phys. Med. Biol.* (1996) vol. 41; pp. 83-91.

J.M. Balter et al.; "Uncertainties in CT-Based Radiation Therapy Treatment Planning Associated With Patient Breathing"; *Int. J. Radiat. Oncol. Biol., Phys.* 36; pp. 167-174 (Aug. 1996).

S.C. Davies et al.; "Ultrasound Quantitation Of Respiratory Organ Motion in The Upper Abdomen"; *Br. J. Radiol.* 67; pp. 1096-1102 (Nov. 1994).

R.L. Ehman el al.; "Magnetic Resonance Imaging With Respiratory Gating: Techniques and Advantages"; *Am. J. Roentgenol* 143; pp. 1175-1182 (Dec. 1984).

H. Frölich et al.; "A Simple Device For Breath-Level Monitoring During CT"; *Radiology* 156; p. 235 (Jul. 1985).

R.M. Henkelman et al.; "How Important Is Breathing In Radiation Therapy Of The Thorax?"; *Int. J. Radiat. Oncol., Biol., Phys.* 8; pp. 2005-2010 (Nov. 1982).

M.B.M. Hofman et al.; "MRI Of Coronary Arteries: *2D Breath-Hold* vs. *3D Respiratory-Gated Acquisition*"; *J. of Comp. Assisted Tomography* 19: pp. 56-62 (Jan./Feb. 1995).

G.J. Kutcher et al.; "Control; Correction, and Modeling Of Setup Errors and Organ Motion", *Semin. Radiat. Oncol.* 5; pp. 134-145 (Apr. 1995).

J. Hanley et al.; "Deep Inspiration Breath-Hold Technique for Lung Tumors: The Potential Value of Target Immobilization And Reduced Lung Density In Dose Escalation"; *Int. J. Radiat. Oncol., Biol. Phys.* 45; pp. 603-611 (Oct. 1999).

L.S. Johnson et al.; "Initial Clinical Experience With A Video-Based Patient Positioning System"; *Int. J. Radiat. Oncol. Biol. Phys.* 45; pp. 205-213; (Aug. 1999).

H.W. Korin et al.; "Respiratory Kinematics Of The Upper Abdominal Organs: A Quantitative Study"; *Magn. Reson. Med.* , 23; pp. 172-178 (Jan. 1992).

H.D. Kubo et al.; "Respiration Gated Radiotherapy Treatment: A Technical Study"; *Phys. Med. Biol.* 41; pp. 83-91; (1996).

H.D. Kubo et al.; "Potential And Role Of A Prototype Amorphous Silicon Array Electronic Portal Imaging Device In Breathing Synchronized Radiotherapy"; *Med. Phys.* 26; pp. 2410-2414; (Nov. 1999).

C.E. Lewis et al.; "Comparison Of Respiratory Triggering And Gating Techniques For The Removal Of Respiratory Artifacts In MR Imaging"; *Radiology* 160; pp. 803-810; (Sep. 1986).

D. Li et al.; "Coronary Arteries: Three-Dimensional MR Imaging With Retrospective Respiratory Gating"; *Radiology* 201; pp. 857-863 (Dec. 1996).

M.A. Moerland et al.; "The Influence Of Respiration Induced Motion Of The Kidneys On The Accuracy Of Radiotherapy Treatment Planning, A Magnetic Resonance Imaging Study", *Radiotherapy Oncol.* 30, pp. 150-154 (1994).

K. Ohara et al.; "Irradiation Synchronized With Respiration Gate"; *Int. J. Radiat. Oncol., Biol. Phys.* 17; pp. 853-857; (Oct. 1989).

J.N. Oshinski et al.; "Two-Dimensional Coronary MR Angiography Without Breath Holding"; *Radiology* 201; pp. 737-743; (Dec. 1996).

C.R. Ramsey et al.; "A Comparison Of Beam Characteristics For Gated And Nongated Clinical X-Ray Beams"; *Med. Phys.* 26; pp. 2086-2091; (Oct. 1999).

C.R. Ramsey et al.; "Clinical Efficacy Of Respiratory Gated Conformal Radiation Therapy", *Medical Dosimetry* 24; pp. 115-119: (1999).

F. Lethimonnier et al.; "Three-Dimensional Coronary Artery MR Imaging Using Prospective Real-Time Respiratory Navigator and Linear Phase Shift Processing: Comparison With Conventional Coronary Angiography", *Magn. Reson. Imaging* 17; pp. 1111-1120; (1999).

R.J. van Geuns et al.; "Magnetic Resonance Imaging Of The Coronary Arteries: Clinical Results From Three Dimensional Evaluation Of A Respiratory Gated Technique"; *Heart* 82: pp. 515-519; (Oct. 1999).

C.J. Ritchie et al.; "Predictive Respiratory Gating: A New Method To Reduce Motion Artifacts On CT Scans"; *Radiology* 1990; pp. 847-852; (Mar. 1994).

R.D. Rogus et al.; "Accuracy Of A Photogrammetry-Based Patient Positioning and Monitoring System For Radiation Therapy"; *Med. Phys.* 26; pp. 721-728; (May 1999).

K. Cho et al.; "Development Of Respiratory Gated Myocardial SPECT System", *J. Nucl. Cardiol.* 6; pp. 20-28; (Jan./Feb. 1999).

C.S. Ross et al.; "Analysis Of Movement Of Intrathoracic Neoplasms Using Ultrafast Computerized Tomography"; *Int. J. Radiat. Oncol., Biol., Phys.* 18; pp. 671-677; (Mar. 1990).

V.M. Runge et al; "Respiratory Gating In Magnetic Resonance Imaging at 0.5 Tesla"; *Radiology* 151; pp. 521-523; (May 1984).

T.S. Sachs et al; "Real-Time Motion Detection In Spiral MRI Using Navigators", *Magn. Reson. Med.* 32; pp. 639-645; (Nov. 1994).

L.H. Schwartz et al; "Kidney Mobility During Respiration"; *Radiother. Oncol.* 32; pp. 84-86; (1994).

M. Paivansalo Suramo et al.; "Cranio-caudal Movements Of The Liver, Pancreas And Kidneys In Respiration", *Acta Radiol. Diagn.* 2; pp. 129-131; (1984).

C.R. Ramsey et al.; "Clinical Efficacy Of Respiratory Gated Conformal Radiation Therapy"; *Med. Dosim.* 24; pp. 115-119; (1999).

J.W. Wong et al.; "The Use Of Active Breathing Control (ABC) To Reduce Margin For Breathing Motion"; *Int. J. Radiat. Oncol., Phys.* 44; pp. 911-919; (Jul. 1999).

H.D. Kubo et al.; "Compatibility Of Varian 2100C Gated Operations With Enhanced Dynamic Wedge And IMRT Dose Delivery"; *Med. Phys.* 27; pp. 1732-1738; (Aug. 2000).

H. Shirato et al.; "Four-Dimensional Treatment Planning And Fluroscopic Real-Time Tumor Tracking Radiotherapy For Moving Rumor"; *Int. J. Radiat. Oncol., Biol., Phys.* 48; pp. 435-442; (Sep. 2000).

N.G. Bellenger et al.; "Left Ventricular Quantification In Heart Failure By Cardiovascular MR Using Prospective Respiratory Navigator Gating: Comparison With Breath-Hold Acquisition"; *J. Magn. Reson. Imaging* 11: pp. 411-417; (Apr. 2000).

Q. Yuan et al.; "Cardiac-Respiratory Gating Method For Magnetic Resonance Imaging Of The Heart"; *Magn. Reson. Med.* 43; pp. 314-318; (Feb. 2000).

K.E. Rosenzweig et al.: "The Deep Inspiration Breath Hold Technique In The Treatment Of Inoperable Non-Small Cell Lung Cancer"; *Int. J. Radiat. Oncol., Biol., Phys.* 48; pp. 81-87; (Aug. 2000).

D. Mah et al.; "Technical Aspects Of The Deep Inspiration Breath Hold Technique In The Treatment Of Thoracic Cancer"; *Int. J. Radiat. Oncol., Biol., Phys.* 48; pp. 1175-1185; (Nov. 2000).

G.S. Mageras et al.; "Respiratory Motion-Induced Treatment Uncertainties"; *Patras Medical Physics 99—VI International Conference On Medical Physics, Monduzzi Editore*; pp. 33-39; (Sep. 1999).

G.S. Mageras; "Interventional Strategies For Reducing Respiratory-Induced Motion In External Beam Therapy"; *The Use of Computers in Radiation Therapy XIIIth International Conference, Heidelberg, Germany*; pp. 514-516; (May 2000).

S. Malone et al.; "Respiratory-Induced Prostate Motion: Quantification And Characterization", *Int. J. Radiat. Oncol., Biol., Phys.* 48; pp. 105-109; (Aug. 2000).

G. Mageras et al.; "Initial Clinical Evaluation Of A Respiratory Gating Radiotherapy System"; $22^{nd}$ *Annual EMBS International Conference*, Chicago, IL.; pp. 2124-2127; (Jul. 23-28, 2000).

Ellen Yorke et al.; "Respiratory Gating Of Sliding Window IMRT"; $22^{nd}$ *Annual EMBS International Conference, Chicago, IL.*; pp. 2118-2121; (Jul. 23-28, 2000).

Jolesz, Ferenc M.D., et al.; "Image-Guided Procedures And The Operating Room Of The Future"; *Radiology; SPL Technical Report #48*; May 1997: 204:601-612.

Mostafavi, Hassan; "Overview of Post-Processing Algorithm to Create Volumetric Motion Sequences"; Varian Medical Systems, Inc.; May 2, 2002.

Mostafavi, Hassan; "Method and System for Radiation Application"; U.S. Appl. No. 10/678,741; filed Oct. 3, 2003; Specification 63 pgs.; Claims 9 pgs; Abstract 1 pg; Drawings 20 pgs.

U.S. Appl. No. 09/893,122, filed Jun. 26, 2001, Mostafavi.

* cited by examiner

| Exam ID | Patient ID |
| Series # | Patient Name |
| Image # | Exam Date |
| | |
| Slice Location: | Width |
| Slice Thickness | Level |
| | Phase% |

SYSTEMS AND METHODS FOR IMPROVING USABILITY OF IMAGES FOR MEDICAL APPLICATIONS

CROSS REFERENCE TO RELATED APPLICATIONS

This application claims the priority of U.S. Provisional Patent Application Ser. No. 60/415,992 filed Oct. 5, 2002, which is hereby incorporated by referenced in its entirety.

BACKGROUND OF THE INVENTION

This invention relates generally to images used in medical applications, and more particularly to methods and apparatus for improving usability of images for medical applications.

As a patient breathes, organs move within the chest and abdominal cavity of the patient. If images are acquired while the patient is breathing anatomical information in a slice of image of the patient may be blurred and not clinically useful. Multiple acquisitions and short breathe holds are used to determine organ motion. Multiple acquisitions and short breathe holds are also used to obtain images with little or no respiratory motion. The extent of organ motion during a respiratory cycle is not easily determinable in a consistent manner. As a result, an organ, which should be treated, is sometimes not treated with a maximum amount of radiation or surrounding organs are exposed to unneeded radiation due to respiratory motion of the patient. Accordingly, it would be desirable to be able to collect data while the patient is breathing and then sort data to the same point in the respiratory cycle thereby freezing motion which would otherwise blur anatomical information in the data. It would also be desirable to provide information about the location of an organ in relationship to other organs at a point in the respiratory cycle.

BRIEF DESCRIPTION OF THE INVENTION

In one aspect, a method for retrospective internal gating is provided. The method includes scanning a patient to obtain projection data, generating images from the projection data, generating a signal representing information regarding a physiological cycle of an object within the patient, specifying at least one target phase based on which the images can be sorted, and sorting the images based on the target phase within a cycle of motion of the object to generate at least one series of images.

In another aspect, a system for imaging a moving object within a patient is provided. The system includes a computed tomography (CT) scanner configured to acquire projection data of the patient, an image reconstructor coupled to the CT scanner and configured to generate images corresponding to the projection data, a device coupled to the scanner and configured to generate a signal representing information regarding a motion of the object; and a controller coupled to the image reconstructor. The controller is configured to enable a user to specify at least one target phase and sort the images based on the target phase within a cycle of the motion of the object to generate at least one series of images.

In yet another aspect, a system for imaging a moving object within a patient is provided. The system includes a computed tomography (CT) scanner configured to acquire projection data of the patient, an image reconstructor configured to generate images corresponding to the projection data, a device configured to generate a signal representing information regarding a motion of the object, and a controller. The controller is configured to enable a user to specify at least one target phase and sort the images based on the target phase within a cycle of the motion of the object to generate at least one series of images.

In still another aspect, a computer is provided. The computer is configured to instruct a scanner to acquire projection data of the patient, instruct an image reconstructor to generate images corresponding to the projection data, instruct a device to generate a signal representing information regarding a motion of the object, enable a user to specify at least one target phase, and sort the images based on the target phase within a cycle of the motion of the object to generate at least one series of images.

In another aspect, a computer-readable medium encoded with a program is provided. The program is configured to instruct a scanner to acquire projection data of the patient, instruct an image reconstructor to generate images corresponding to the projection data, instruct a device to generate a signal representing information regarding a motion of the object, enable a user to specify at least one target phase, and sort the images based on the target phase within a cycle of the motion of the object to generate at least one series of images.

BRIEF DESCRIPTION OF THE DRAWINGS

FIG. 9 shows an annotation of an image that is generated using the PET/CT system.

FIG. 11 shows an embodiment of a popup window that is displayed when a "Save Series" button is selected on the image review screen.

DETAILED DESCRIPTION OF THE INVENTION

Figure 1:
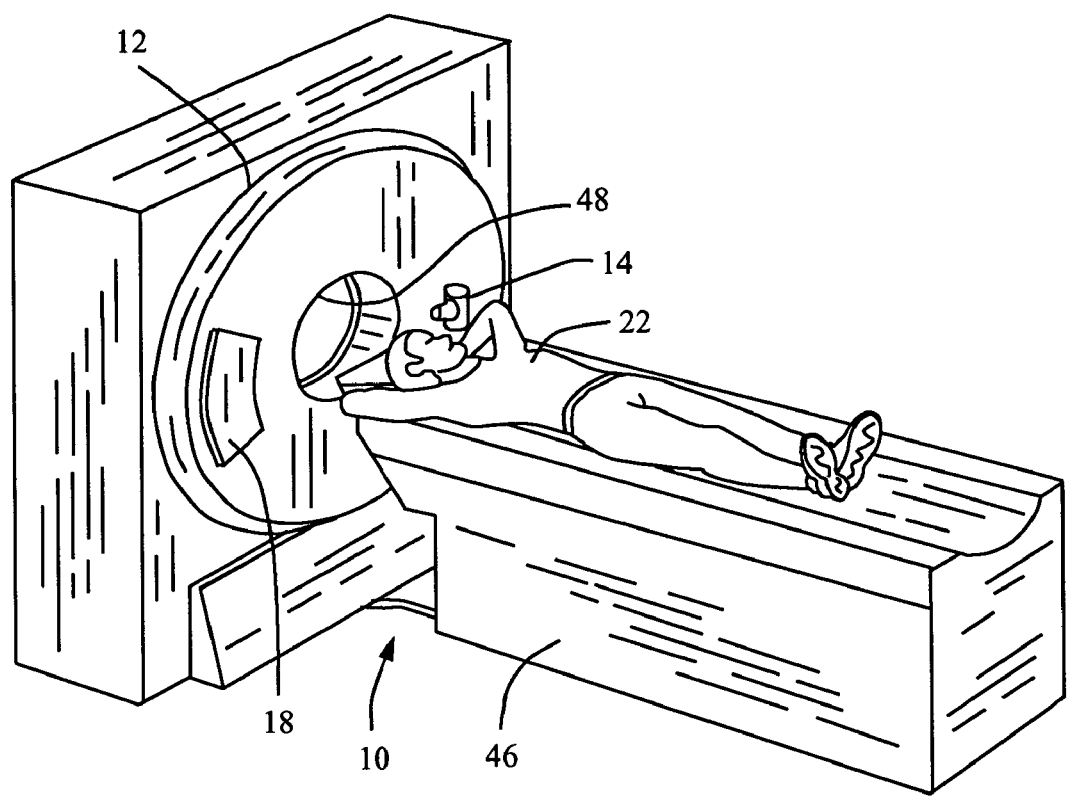
FIG. 1 is a perspective an embodiment of a positron emission tomography/computed tomography (PET/CT) system in which systems and methods for improving usability of images for medical applications are implemented.

In computed tomography (CT) imaging system configurations, an X-ray source projects a fan-shaped beam which is collimated to lie within an X-Y plane of a Cartesian coordinate system and generally referred to as an "imaging plane". The X-ray beam passes through a subject, such as a patient, being imaged. The beam, after being attenuated by the subject, impinges upon an array of radiation detectors. The intensity of the attenuated radiation beam received at the detector array is dependent upon the attenuation of an X-ray beam by the subject. Each detector element of the array produces a separate electrical signal that is a measurement of the beam intensity at the detector location. The intensity measurements from all of the detectors are acquired separately to produce a transmission profile.

In third generation CT systems, the X-ray source and the detector array are rotated with a gantry within the imaging plane and around the subject to be imaged such that the angle at which the X-ray beam intersects the subject constantly changes. A group of X-ray attenuation measurements, i.e., projection data, from the detector array at one gantry angle is referred to as a "view". A "scan" of the subject comprises a set of views made at different gantry angles, or view angles, during one revolution of the X-ray source and detector. Examples of a scan include an axial scan, a cine scan, and a helical scan.

In an axial scan, the projection data is processed to construct an image that corresponds to a 2-dimensional (2D) slice taken through the subject. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display. Positron emission tomography (PET) scanners incorporate a process similar to that found in CT, in that a map or the subject attenuation can be generated. A method to perform this attenuation measurement includes use of rotation rod sources containing positron-emitting radionuclides. The rods rotate outside the patient bore, but inside the diameter of the PET detector ring. Annihilation events occurring in the rods can send one photon into a near-side detector while the pair photon traverses an object of interest, such as, for instance, lung or heart, of the subject, in a manner similar to the CT X-ray. The data found from this method contains essentially the same information as that found from the CT method except for the statistical quality of the resultant data. In the rotating rod case, the statistical quality is orders of magnitude inferior to most common CT scans. For the PET purpose, data acquired in this manner is used to correct for the attenuation seen in the subject by the 511 keV photons, which is often the most substantial correction performed on the PET data. In a cine scan, the projection data is processed to construct a 2-dimensional (2D) or a 3-dimensional (3D) slice taken through the patient.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two dimensional slice taken through the subject.

At least some CT systems are configured to also perform Positron Emission Tomography (PET) and are referred to as PET/CT systems. Positrons are positively charged electrons (anti-electrons) which are emitted by radio nuclides that have been prepared using a cyclotron or other device. The radionuclides most often employed in diagnostic imaging are fluorine-18 ($^{18}$F), carbon-11 ($^{11}$C), nitrogen-13 ($^{13}$N), and oxygen-15 ($^{15}$O). Radionuclides are employed as radioactive tracers called "radiopharmaceuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, which is to be imaged. It is known that specific radiopharmaceuticals become concentrated within certain organs. The process of concentrating often involves processes such as glucose metabolism, fatty acid metabolism and protein synthesis.

After the radiopharmaceutical becomes concentrated within an organ and while the radionuclides decay, the radionuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using PET. First, each gamma ray has an energy of approximately 511 keV upon annihilation. Second, the two gamma rays are directed in nearly opposite directions.

In PET imaging, if the general locations of annihilations can be identified in three dimensions, a 3-dimensional (3D) image of radiopharmaceutical concentration in an organ can be reconstructed for observation. To detect annihilation locations, a PET camera is employed. An exemplary PET camera includes a plurality of detectors and a processor which, among other things, includes coincidence detection circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes millions of annihilations are recorded, each annihilation associated with a unique detector pair. After an acquisition period, recorded annihilation data can be used via any of several different well known image reconstruction methods to reconstruct the 3D image of the organ.

As used herein, an element or step recited in the singular and preceded with the word "a" or "an" should be understood as not excluding plural the elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable mages and data representing a viewable image. However, many embodiments generate (or are configured to generate) at least one viewable image.

Figure 2:
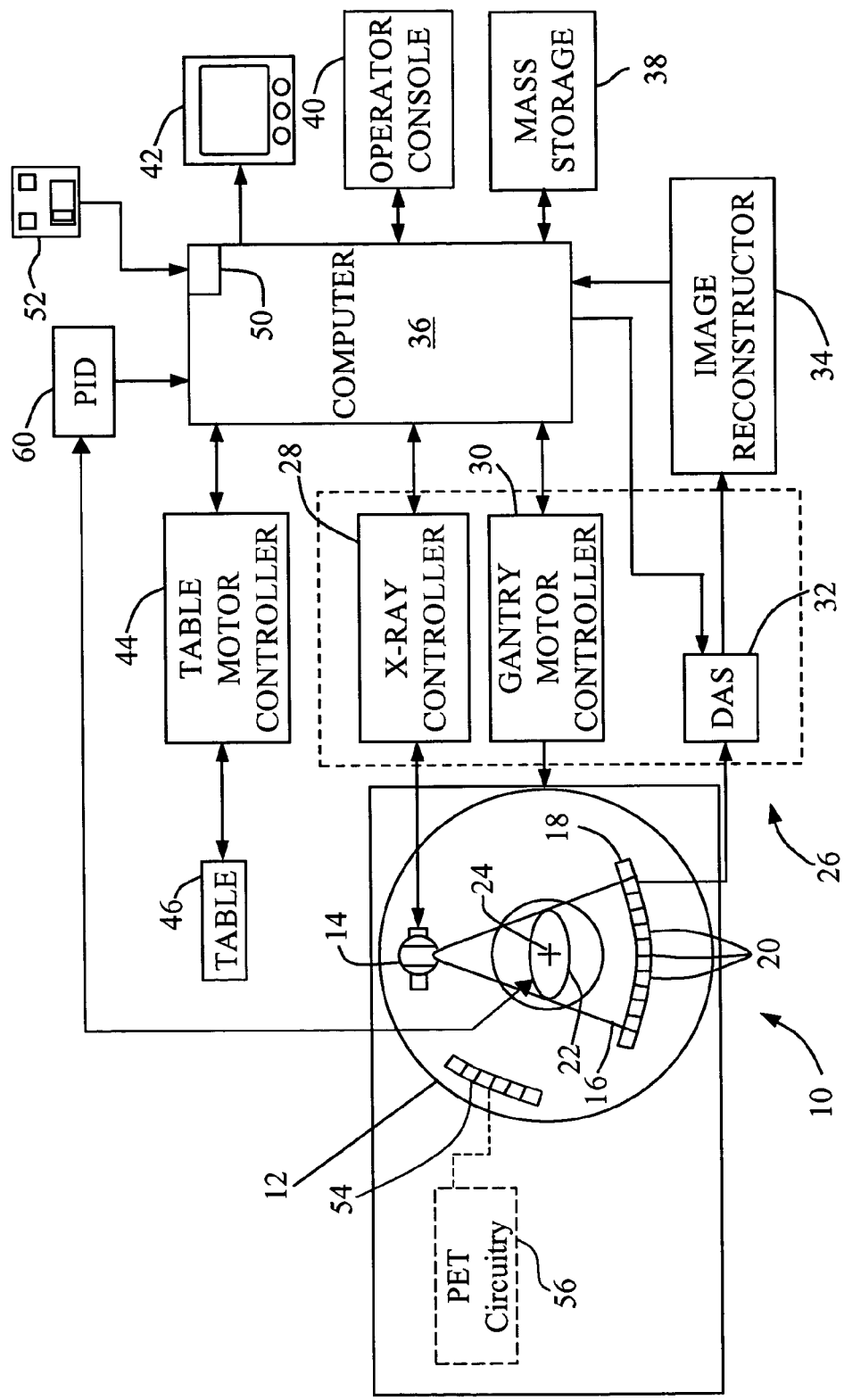
FIG. 2 is a block diagram of the PET/CT system of FIG. 1.

Referring to FIGS. 1 and 2, a multi-slice scanning imaging system, for example, a CT imaging system, is shown as including a gantry 12 representative of a "third generation" CT imaging system. Gantry 12 has an X-ray source 14 that projects a beam of X-rays 16 toward a detector array 18 on the opposite side of gantry 12. Detector array 18 is formed by a plurality of detector rows (not shown) including a plurality of detector elements 20 which together sense the projected X-rays that pass through a subject, such as a medical patient 22. Each detector element 20 produces an electrical signal that represents the intensity of an impinging X-ray beam and hence allows estimation of the attenuation of the beam as it passes through patient 22. During a scan to acquire X-ray projection data, gantry 12 and the components mounted thereon rotate about a center of rotation 24.

It is noted that a CT imaging system can be combined with a PET imaging system to form a PET/CT imaging system 10. In one embodiment, PET/CT imaging system 10 includes a plurality of PET detectors 54, rotating rod sources (not shown) and a PET circuitry 56 within gantry 12. An example of such as PET/CT system is a Discovery LS PET/CT system commercially available from General Electric Medical Systems, Waukesha, Wis. In another embodiment, a PET/CT imaging system includes the plurality of PET detectors 54 and PET circuitry 56 located with a separate gantry. An example of such a PET/CT system is a Discovery ST system commercially available from General Electric Medical Systems. In yet another embodiment, PET/CT imaging system 10 scans to provide 4-dimensional (4D) CT images.

FIG. 2 shows only a detector row of detector elements 20. However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of X-ray source 14 are governed by a control mechanism 26 of PET/CT system 10. Control mechanism 26 includes an X-ray controller 28 that provides power and timing signals to X-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized X-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Computer 36 is electrically coupled to a physiological information device (PID) 60 to identify or determine, a physiological cycle of an object, such as, heart or lungs, of patient 22. More specifically, PID 60 is coupled to computer 36 and generates a physiological cycle signal representative of respiration, including a plurality of phases, of patient 22. The physiological cycle signal that is representative of respiration of patient 22 is referred to as a respiratory signal.

In one embodiment, information associated with the respiratory signal of patient 22 is stored in a text file. The text file includes a header section and a data section. The header includes patient ID, date, time, total study time, samples per second, number of respiratory cycles, and number of phases in a cycle. The data section includes a digitized value of the respiratory signal, X-ray number, mark, and phase. Examples of marks include G, GZ, O, OZ, E, and EZ, where G indicates that X-Ray source 14 is turned on, Z represents phase 0, O indicates that X-Ray source 14 is turned off, and E represents end of the text file. An example of a suffix of the text file is ".vxp". In another embodiment, the text file includes no space character. In yet another embodiment, tags of the text file that are kept constant are header, data, cyclical redundancy check (CRC), version, data_layout, Patient_ID, Date, Total_study_time, Samples_per_second, amplitude, phase, timestamp, validflag, ttlin, and mark, where Samples_per second is an integer, amplitude is a float value, phase is a float value, timestamp is an integer, validflag is an integer, ttlin is an integer value, a tag value delimiter is "=", a data layout delimiter is ",", a date delimiter is "–", the mark is "Z" or "P", and a timestamp is in milliseconds. In the yet another embodiment, if ttlin is 0, X-Ray source 14 is turned on and if ttlin is 1, X-Ray source 14 is turned off. Alternatively, if ttlin is 1, X-Ray source 14 is turned on and if ttlin is 0, X-Ray source 14 is turned off. The respiratory signal is stored in a computer-readable medium 52, which is described in detail below.

In one embodiment, computer 36 includes a device 50, for example, a floppy disk drive or CD-ROM drive, for reading instructions and/or data from computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Although the specific embodiment mentioned above refers to a third generation CT system coupled with PET system, methods for improving usability of images for medical applications equally apply to fourth generation CT systems that have a stationary detector and a rotating X-ray source, fifth generation CT systems that have a stationary detector and an X-ray source.

Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro PET and CT systems which are sized to study lab animals as opposed to humans.

Figure 3:
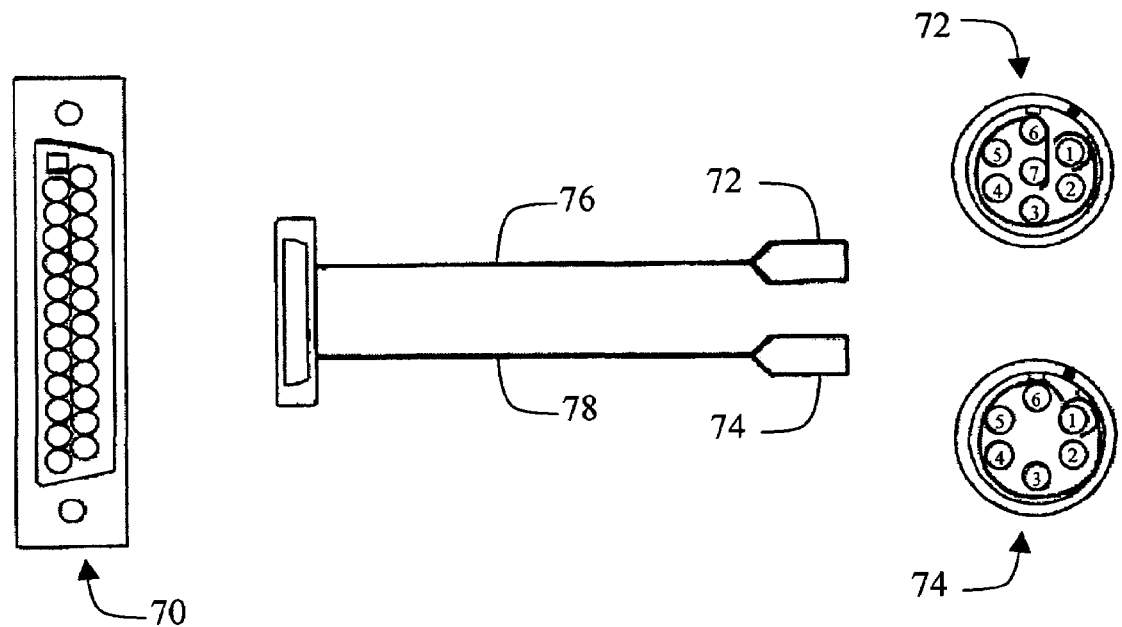
FIG. 3 is a block diagram of connectors that are used to couple a computer and a physiological information device (PID) of the PET/CT system of FIGS. 1 and 2.

FIG. 3 is a block diagram of connectors 70, 72, and 74 between PID 60 and computer 36. Connector 70 is coupled to connectors 72 and 74 via connections 76 and 78, such as cables with each cable having a length of 450 millimetres (mm). An example of connector 72 includes a cardiac lemo connector and an example of connector 74 includes a pulmonary lemo connector. The following table shows functions of pin outs 1-6 of connectors 72 and 74.

TABLE 1

| Pin Number | Signal Description |
| --- | --- |
| 1 | Not used |
| 2 | Not used |
| 3 | X-ray_on(Resp_mon) |
| 4 | X-ray_on_rtn(Resp_mon_rtn) |
| 5 | Resp_trigger |
| 6 | Resp_trigger_rtn |

Figure 4:
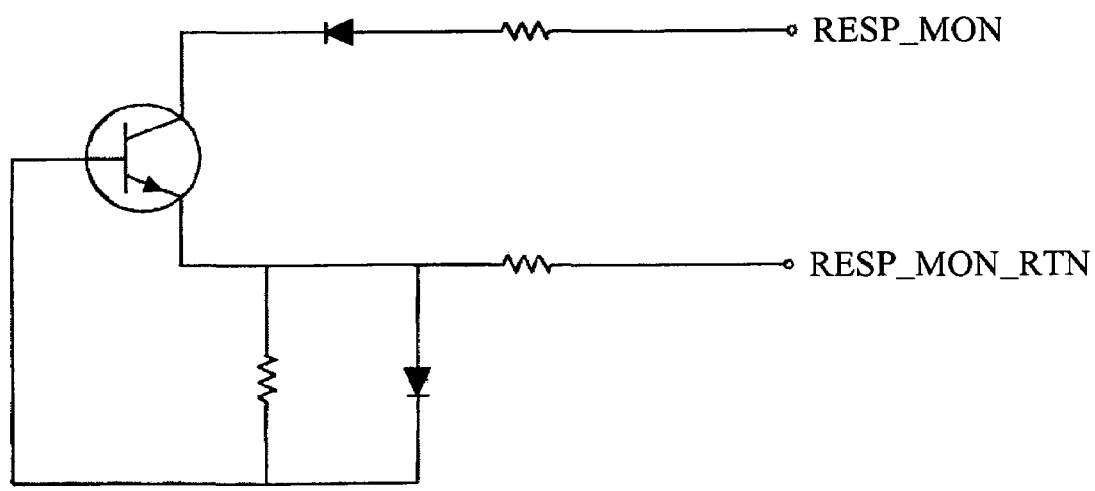
FIG. 4 is a circuit diagram of a circuit for receiving Resp_mon signals from the PID and sending Resp_mon_rtn signals to the PID of FIG. 3.

FIG. 4 is a circuit diagram of a circuit for receiving Resp_mon signals from PID 60 and sending Resp_mon_rtn signals to PID 60. The circuit is located with computer 36.

The user can launch the method for improving usability of images for medical applications from a browser by selecting images of objects within patient 22 obtained using PET/CT system 10. The user can load a subset of the images by selecting some of the images in the browser before launching the method. In one embodiment, images corresponding to multiple patients are not loaded. If images corresponding to multiple patients are selected in the browser, an error messages is posted to inform the user of such an error and the method exits. Upon loading images, the method ensures that the images comply with a particular standard. If the standard is not met, a proper error message is posted to inform the user of the specific error and the method is terminated due to error. Moreover, upon loading images, the method ensures that there are at least a certain number of images, such as, for instance, 5 images, that are selected in the browser. Otherwise, a message is posted to inform the user and the method terminates. Furthermore, upon loading images, the method ensures that a scan mode for the images selected in the browser is valid. For instance, upon loading images, the method validates that cine and helical modes are used to obtain images. If the scan mode is not valid, an error message is posted to inform the user of the error and the method ends.

Additionally, upon loading images, the method ensures that images selected in the browser are acquired from a particular scanner, such as, for instance, CTi, H1, H2, H3, H4 or Pacific Star, manufactured by General Electric Company. If the Scanner Type is not supported, a message is posted to inform the user of the error. In another embodiment, there is a verification or a validation whether projection data is generated by a scanner manufactured by General Electric Company. In the embodiment, the method does not verify or validate projection data generated by a scanner not manufactured by a specific manufacturer. In another embodiment, the method does not verify or validate projection data generated by a scanner not manufactured by a specific manufacturer unless information regarding acquisition times of images generated using a scanner not manufactured by the manufacturer can be obtained from header of the images.

Moreover, upon loading images, the method ensures that each patient's identification number (ID) on each image header matches with patient IDs stored on computer-readable medium 52. Computer-readable medium 52 is present in device 50 at the time the method is launched by selecting the browser. In the case of patient ID mismatch due to an incorrect ID, there is a message to inform the user of the problem and the user is enabled to re-load another respiratory signal or to abort loading the other respiratory signal. To re-load the other respiratory signal, the user inserts a different computer-readable medium with a correct respiratory signal and selects a "Retry" button. In the case where the user decides to proceed further, the user selects a "Continue" button. If the user chooses to continue, the existing respiratory signal, which has the incorrect Patient ID, is used.

After the method is launched, a study screen is displayed with the following patient demographic fields:

TABLE 2

| Field Name | Type/Format | Editable? |
|---|---|---|
| Patient ID* | Label | No |
| Patient Name* | Label | No |
| Exam Date* | Text/YYYYMMDD | No |
| Birth Date* | Numeric text/YYYYMMDD | No |
| Age* | Numeric text | No |
| Gender* | Toggle button | No |
| Weights* | Numeric text | No |

TABLE 2-continued

| Field Name | Type/Format | Editable? |
|---|---|---|
| Referring physician* | Free text | No |
| Radiologist* | Free text | No |
| History* | Free text | No |
| Study notes | Free text | Yes |
| Prepared by | Free text | Yes |

All patient demographic fields denoted as "*" are pre-filled with information available on image header of images selected in the browser. If the contents of a patient demographic field are empty, the patient demographic field is left empty. If the "Age" field is empty, it is computed based on the "Birth Date" field if available. Otherwise, the "Age" field is empty. In one embodiment, all patient demographic fields on the study screen are not editable except for the "Study notes" and "Prepared by" fields. The user is able to add comments in the "Study notes" and "Prepared by" Fields. In another embodiment, there is a button labeled "Create Text Page" on the study screen. The "Create Text Page" button allows the user to create a secondary screen capture image, which captures any text in "Study notes" and "Prepared by" and captures patient ID, patient name, exam number, and original series number. The secondary screen capture follows all restrictions, such as, for example, series description or series number convention, as any normal screen capture used in the method.

Figure 5:
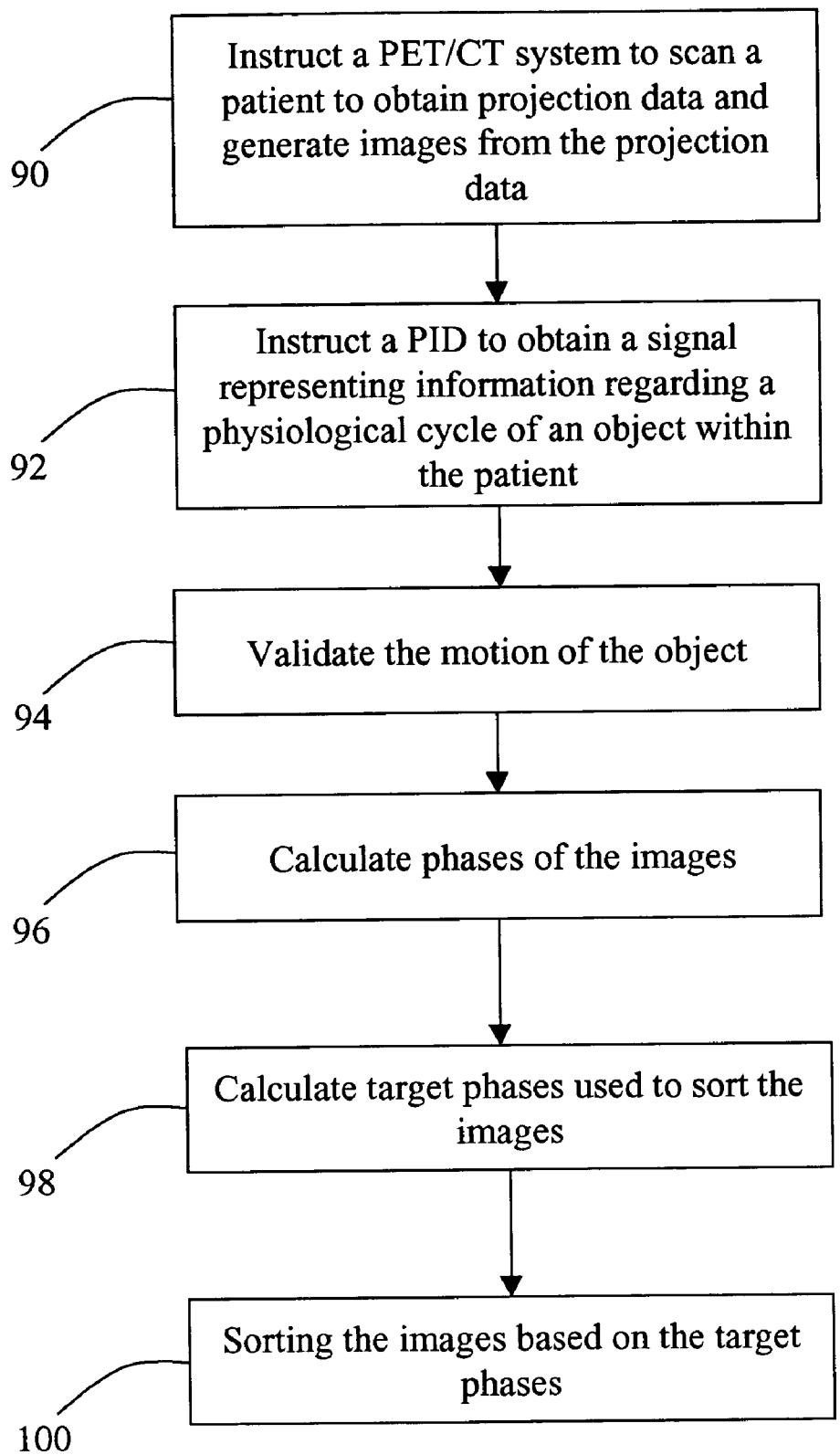
FIG. 5 is a flowchart of an embodiment of a method for improving usability of images for medical applications.

FIG. 5 is a flowchart of an embodiment of a method for improving usability of images for medical applications. Computer 36 executes the method after obtaining images from image reconstructor 34 and after receiving a physiological cycle signal, such as a respiratory signal of patient 22 from PID 60. It is noted that in an alternative embodiment, computer 36, computer-readable medium 52, console 40, and display 42 are located across a network, such as a local area network or a wide area network, from remaining components of PET/CT system 10. In the alternative embodiment, the method is saved in storage device 38 by image reconstructor 34 and is communicated across the network to computer 36. Moreover, in the alternative embodiment, the physiological signal is saved in computer-readable medium 52, which is transported across the network, and the method is accessed from computer-readable medium 52 by using computer 36.

The method includes instructing 90 PET/CT system 10 to scan patient 22 to obtain projection data and generate images from the projection data. The method further includes instructing 92 PID 60 to obtain a physiological cycle signal of an object within patient 22. The method also includes validating 94 the motion of the object and calculating 96 phases of the images. As an example, the respiratory signal from patient 22 is validated by determining whether amplitudes and periods of respiratory cycles of the respiratory signal lie within a percentage. An example of a respiratory signal is a respiratory signal having 12 respiratory cycles/second, which can be used as a default value. An illustration of variation of periods of respiratory cycles is a 0.5 second variation on an average respiratory cycle of 4 second. Large variations in the amplitudes could potentially cause a misregistration of location of the object. Moreover, large variations in the periods could potentially cause a misalignment of phases which could cause a gap in images selected using an automatic image selection described below. However, the magnitudes of periods and the amplitudes are settings in PID 60 and are controllable by the user. Furthermore, since PID 60 has an ability to detect the variations in the periods, variations in the amplitudes, and records confidence levels of respiratory sample points of the respiratory signal, the motion of the object may not be validated. Moreover, as described later, the confidence levels are considered when a phase of each image is computed. In addition, since the respiratory signal includes data during patient 22's preparation prior to scanning patient 22, all respiratory sample points prior to a first time the X-Ray source 14 is turned on are excluded. All calculations described as a part of the method are done with respiratory sample points acquired when X-Ray source 14 is turned on.

The method further includes calculating 98 target phases that can be used to sort images obtained using PET/CT system 10 and sorting 100 the images based on the target phases. Target phases are calculated by computing an average delta phase, which is a sum of phase differences between phases of consecutive images in all cine scans of patient 22 divided by a total number of images in all the cine scans. A number of phases is computed by dividing $2\pi$ by the average delta phase. The automatic image selection, described below, is performed by specifying a phase of a first image in a first cine scan of patient 22 as a target phase. The automatic image selection results in a set of images and phases of the images in the set are averaged to calculate an average phase. The average phase is used as a starting target phase. Subsequent target phases are calculated as a sum of a previous target phase and the average delta phase. All target phases can be sorted in an incremental or a decremental fashion.

Figure 6:
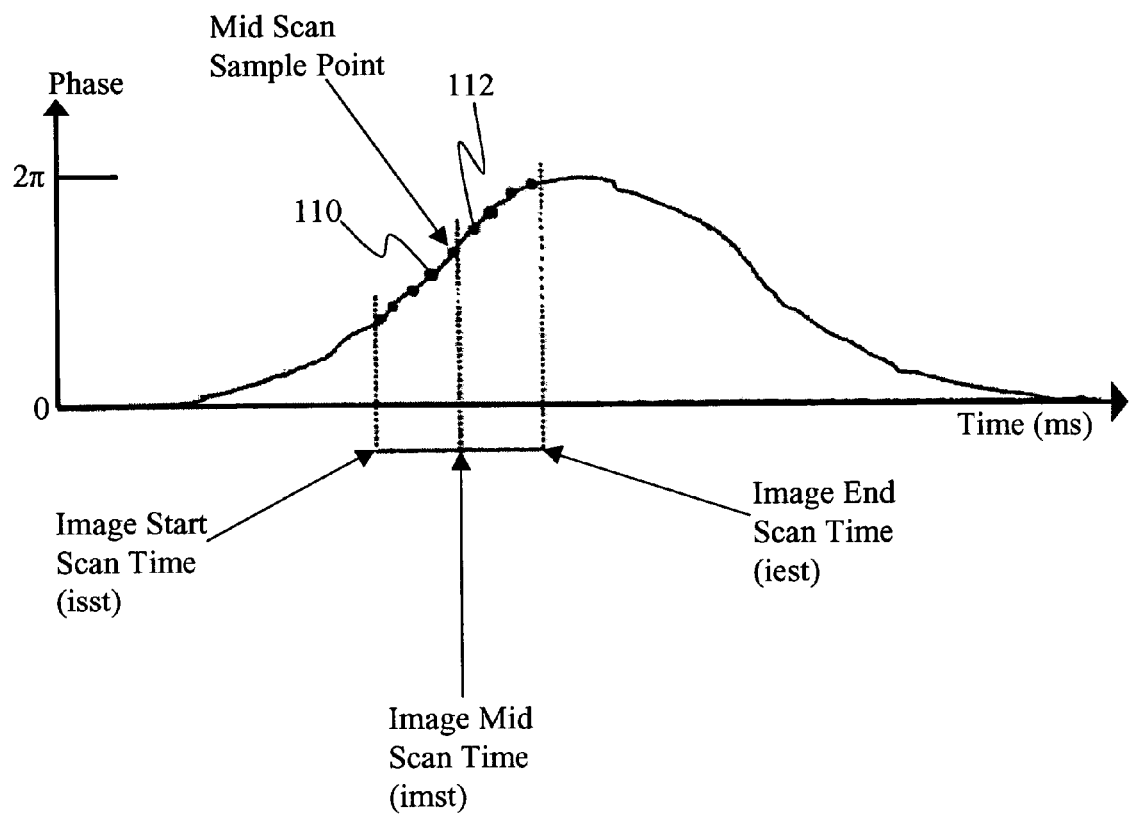
FIG. 6 is a graph illustrating an embodiment of a step of calculating phases in the method.

FIG. 6 shows a graph illustrating an embodiment of step 96 of calculating phases. Step 96 includes reading, from an image header of each image, spatial location at which each image is obtained and a delta start time, which is a time difference between a time at which X-ray source 14 is turned on and a time of image acquisition. Step 96 further includes obtaining phases of respiratory cycles of the respiratory signal, obtaining X-ray information such as times at which X-Ray source 14 is turned on and off, and obtaining confidence level information that indicates confidence levels of sample points on the respiratory signal. The sample points are referred to as respiratory sample points. The confidence levels are determined by correlating times at which images are acquired using PET/CT system 10 with times at which respiratory sample points are acquired.

Step 96 also includes calculating an image start scan time (isst) for each image, an image mid scan time (imst) for each image, and an image end scan time (iest) for each image. The isst is calculated as follows:

$$\text{isst} = \text{delta start time} + \text{scan start time} \quad (1)$$

where scan start time is a time at which X-ray source 14 is turned on.

The imst is calculated as follows:

$$\text{imst} = \text{delta start time} + \text{scan start time} + (\text{duration}/2) \quad (2)$$

where duration is a time difference between the iest and the isst.

The iest is calculated as follows:

$$\text{iest} = \text{delta start time} + \text{scan start time} + \text{duration} \quad (3)$$

Figure 7:
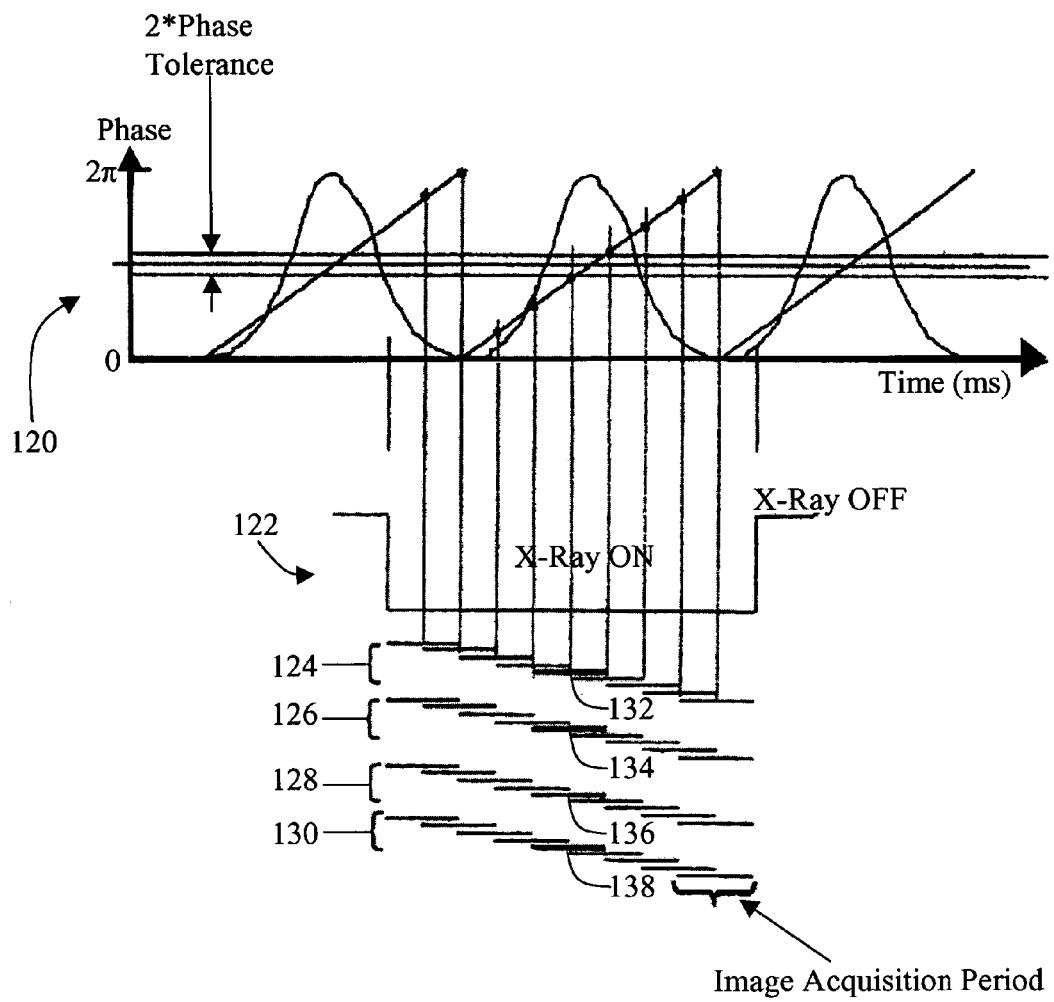
FIG. 7 is a plurality of graphs illustrating a step of sorting images in the method.

The following assumptions are made in calculating the isst, imst, and iest: 1) The scan start time is a time at which an X-ray signal changes from 1 to 0, as shown in FIG. 7, for a first time during a respiratory cycle of the respiratory signal. 2) All other scan start times are obtained in a similar manner by searching times at which an X-ray signal from X-Ray source 14 changes from 1 to 0 during a respiratory cycle of the respiratory signal.

Step 96 further includes obtaining a mid scan sample point for each image. A mid scan sample point satisfies the following conditions: 1) X-Ray source 14 is turned on at a time corresponding to the mid scan sample point, and 2) If the imst is in the middle of two respiratory sample points, a respiratory sample point closest to a scan start time is chose as the mid scan sample point.

Step 96 further includes obtaining respiratory sample points, such as respiratory sample points 110 and 112, located symmetrically around the mid scan sample point. Criteria used to obtain respiratory sample points that are symmetrically located around the mid scan sample point are: 1) X-Ray source 14 is turned on at a time corresponding to a respiratory sample point. 2) Confidence level for the respiratory sample point is non-negative. Such respiratory sample points at which X-Ray source 14 is turned on and confidence level is non-negative are referred to as valid respiratory sample points. 3) A number N of valid respiratory sample points used to calculate a phase of each image are defined via an environmental variable. The environmental variable is referred to as a minimum number of valid respiratory sample points. There also exists another environmental variable, which defines a maximum number of valid respiratory sample points. Alternatively, step 96 includes satisfying the maximum number of valid respiratory sample points. For the purpose of analyzing data corresponding to the respiratory signal, step 96 includes writing to the log file the number of valid respiratory sample points. 4) The respiratory sample points are searched symmetrically from the mid scan sample point outward. If a particular respiratory sample point on one side of the mid scan sample point does not satisfy the confidence level, then the next pair of respiratory sample points is considered on both sides of the mid scan sample point. This means that opposite respiratory sample points on each side of the mid scan sample point should satisfy all the mentioned criteria to be considered valid respiratory sample points. 5) The search for valid respiratory sample points is limited to a total number of respiratory sample points falling within an acquisition period. The total number of respiratory sample points for an image depends on a sampling rate at which the respiratory signal is sampled and duration of the image.

Step 96 further includes calculating a phase for each image. The phase of each image is computed as an average of phases of valid respiratory sample points associated with each image. The phase of each image includes the phase of the mid scan sample point unless confidence level for the mid scan sample point is less than 0. Phases of each respiratory sample point of the respiratory signal range between 0 and $2\pi$. When calculating the phase of each image, phases of each valid respiratory sample point is translated from a 0 to $2\pi$ scale to a 0 to 100 scale. If a valid respiratory sample point cannot be found for an image, the image is a "Phase-Less" image. A "phase-less" image is excluded from the automatic image selection, which is described below. However, the user can also select a "phase-less" image manually.

FIG. 7 is a plurality of graphs illustrating step 100 of sorting images. Graph 120 shows a respiratory signal of patient 22 and graph 122 shows an x-ray signal from X-Ray source 14. Step 100 of sorting images includes grouping images having the same spatial location along a z-axis that lies along a length of patient 22 to form groups and selecting one image in each group. For example, images obtained from a single cine scan by using a detector array in a 4 slice configuration are grouped into 4 groups 124, 126, 128, and 130. As another example, images from a single cine scan are grouped into groups of integral number greater than 0. The number of images in each group obtained from a cine scan are the same. The number of images in each group depends on a duration of a cine scan and depends on time between acquisition of images. According to a scanning protocol, a duration of a cine scan is an average respiratory cycle time of the respiratory cycles of respiratory signal plus one additional second for over scan.

Step 100 of sorting images further includes selecting one image, such as images 132, 134, 136, and 138, in each group satisfying at least one of the following conditions: 1) Phase difference from a target phase should be within a phase tolerance. The phase tolerance is configured via a user interface, described below, to allow the user to modify the phase tolerance for specific needs of the user. Clinically, phase tolerance can be a function of a target phase or other factors. Before there is any projection data acquired, a constant function is applied and a constant can be configured. A value of the phase tolerance is an average delta phase in a first scan performed using PET/CT system 10. The average delta phase is calculated as a sum of phase differences between consecutive images within a respiratory cycle divided by a total number of images in the respiratory cycle. It is noted that the smaller the phase tolerance is, the more likely it is that an image is not selected. 2) If there are two adjacent images, which are within the phase tolerance, the image with a phase closest to the target phase is selected. 3) If there are multiple images within the same z-location, which satisfies condition 1, an image that is near to an imst in a cine scan will be selected. The selection of images, such as images 132, 134, 136, and 138 in each group is the automatic image selection.

The automatic image selection selects images based on a target phase specified by the user and a configurable phase tolerance. However, there are many reasons that could cause an in-contiguity in an image set obtained from the automatic image selection. Examples of the reasons include slow breathe of patient 22, some abnormal occasions during a scan or a very small phase tolerance. In such a scenario, a warning message is posted to inform the user of a slice location at which no image is selectable for a given target phase and a phase tolerance. The user can perform a manual image selection, which overwrites the phase tolerance.

Since PID 60 is not synchronized with a scanner of PET/CT system 10, phases of images in different cine scans are different. However, through the use of a proper inter scan delay (ISD) and time between image acquisitions, phase difference between images belonging to different cine scans is minimized. For example, when the ISD plus an over scan time is an integral multiple of the time between image acquisitions, an ideal condition to obtain congruence between phases of images in different cine scans is achieved.

Figure 8:
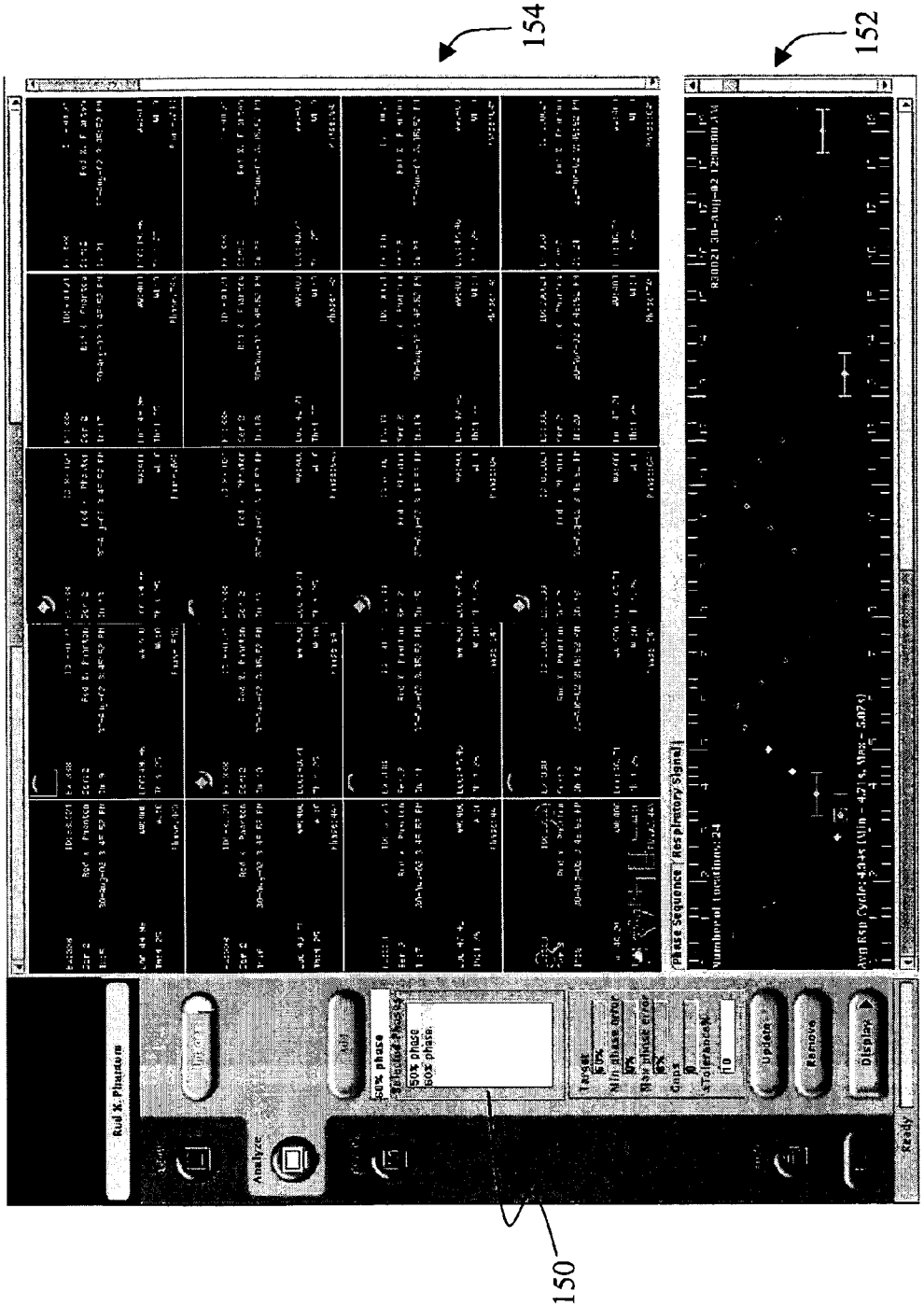
FIG. 8 shows an embodiment of a user interface or an image selection screen that enables the user to select target phases and phase tolerances of images generated using the PET/CT system of FIGS. 1 and 2.

FIG. 8 shows an embodiment of a user interface or an image selection screen that enables the user to select phases and phase tolerances of images. The image selection screen includes a "Potential Target Phase" list (not shown), an "Add" button, an "Update" button, a "Phase List-Select" region 150, a "Remove" button, a "Display" button, a respiratory signal panel 152, an image viewer 154, and a "Help" button. Phase of a respiratory signal of patient 22 is measured along a vertical axis of respiratory signal panel 152 and time is measured along a horizontal axis of respiratory signal panel 152. The user changes the period of a respiratory signal in respiratory signal panel 152 and position of a zero phase pulse of the respiratory signal by moving the vertical axis so that image acquisition appears to start at the zero phase pulse.

When the "Potential Target Phase" list is selected, a list of all possible phases for a current study of patient 22 is displayed. When a target phase is selected by the user in the "Potential Target Phase" list, respiratory signal panel 152 displays all images for the target phase that is selected. In addition, image viewer 154 updates accordingly. The user can over-write the images displayed for the target phase selected by the user by selection of different images on image viewer 154 or on respiratory signal panel 152. Once the user is satisfied with the images selection for a phase selected by the user, the user can save the target phase selected by the user via an "Add" button.

The "Add" button enables the user to create a list of all target phases for reviewing purposes. The "Add" button is only operable when there is a target phase selected by the user on the "Potential Target Phase" list. Every time the "Add" button is selected, a target phase selected by the user via the "Potential Target Phase" list is added to "Phase List-Select" region 150. The phase added to "Phase List-Select" region 150 is highlighted on the "Phase List-Select" region and the "Add" button becomes inoperable. To add another target phase to "Phase List-Select" region 150, the user selects a target phase on the "Potential Target Phase" list and selects the "Add" button again. It is noted that at the time when a phase is added to the "Potential Target Phase" list, there is no generation of corresponding images or storage of the images in storage device 38. To save a series of images in storage device 38, a "Save Series" button described below is selected by the user.

The "Update" button enables the user to update an existing target phase with its associated images. To do so, the user selects a target phase in "Phase List-Select" region 150. A highlighted phase on "Phase List-Select" region 150 is updated accordingly once the user selects the "Update" button. Once an existing target phase is updated, the user can overwrite an image on image viewer 154 or on respiratory signal panel 152 with a different image. The "Update" button is operable when the user selects a target phase in the "Phase List-Select" region 150. When multiple target phases are selected in "Phase List-Select" region 150, the "Update" button is inoperable.

"Phase List-Select" region 150 enables the user to review target phases with its associated images. To view the images associated with a target phase, the user selects the target phase on "Phase List-Select" region 150. Image viewer 154 is updated to show all images belonging to the target phase selected on "Phase List-Select" region 150. In addition, respiratory signal panel 152 is updated to show images for the target phase selected on "Phase List-Select" region 150. In an embodiment, there is a vertical scroll bar to scroll through "Phase List-Select" region 150 if "Phase List-Select" region 150 becomes too extensive to be displayed on a single screen.

The "Remove" button enables the user to remove a target phase from "Phase List-Select" region 150. To remove a target phase, the user selects a target phase in "Phase List-Select" region 150 and clicks on the "Remove" button. When multiple target phases are selected to be deleted, image viewer 154 and respiratory signal panel 152 displays target phases that are selected first by the user among the multiple target phases.

A display menu that is accessed by selecting the "Display" button includes at least one of the following options: 1) An image display format, for example, a 5×4 image display format, a 3×2 image display format, or a 2×1 image display format, where the 5×4 image display format is a default format. 2) An "Annotation On" of an "Annotation Off", where, for example, the "Annotation On" is a default. An example of an annotation of an image is shown in FIG. 9. 3) A "New Respiratory Waveform" option enables the user to load a new respiratory signal. Once the new respiratory signal is loaded, the "Potential Target Phase" list is updated according to the new respiratory waveform. However, any existing phases in "Phase List-Select" region 150 are removed. On loading the new respiratory signal, the method ensures that patient 22's ID for a current study matches that on computer-readable medium 52. If a mismatch occurs, a message is posted to inform the user of such an error. The user has an option of continuing or reloading another respiratory signal by using a different computer-readable medium 52. 4) A phase tolerance text field has a default value that is half of the average delta phase. In one embodiment, the phase tolerance text field is an integer value ranging from 0 to 50. The integer value represents an allowable percentage phase tolerance that is used to perform the automatic image selection. For example, if a target phase value is 50% and a phase tolerance is entered as 20% by the user, any image whose phase ranges from 30% to 70% is selectable. Once the user enters a phase tolerance and selects a "Return/Enter" key on the keyboard of console 40 linked to computer 36, respiratory signal panel 152 is updated to correspond to the phase tolerance. In addition, images for all existing phases are re-selected. Moreover, there is a popup message that suggests the user to review images associated with any previous target phases.

Respiratory signal panel 152 enables visualization of a respiratory signal of patient 22. Images are display as color-coded diamonds on respiratory signal panel 152. As an example, blue diamonds signify images selected using the automatic image selection, white diamonds signify images currently displayed in image viewport, yellow diamonds signify "Phase-less" images, red diamonds denote images selected using the automatic image selection and have been re-selected by the user, and grey diamonds indicate all other images. Position of each diamond on respiratory signal panel 152 indicates a phase of an image.

In addition, the number of phases are represented in a single row on image viewer 154 and number of z locations are represented in a single column on image viewer 154. An average period of respiratory cycles of a respiratory signal, a maximum value of respiratory cycles of the respiratory signal, and a minimum value of respiratory cycles of the respiratory signal are printed on the bottom of respiratory signal panel 152.

A line, such as a red line, signifies a current target phase. To help the user to visualize ranges of the phases selected for a given target phase, there are two horizontal lines showing a maximum phase and a minimum phase. The maximum and minimum phases do not include any information on the "Phase-less" images. The horizontal lines corresponding to maximum and minimum phases are adjusted accordingly as images are manually selected. However, the user is unable to select images outside of a phase tolerance. To select images outside of the phase tolerance, the user increases the phase tolerance. If images for a target phase are not selected, there is a message posted to indicate z locations of such images.

Image viewer 154 enables the user to review images in a display format specified in the display menu described above. Images are displayed in at least one of the following fashions: 1) Images are aligned based on their spatial location as well as their imst. 2) Images in the same horizontal row have the same spatial location. Alternatively, images in the same vertical column have the same spatial location. 3) Images in the same vertical column have the same imst which means they belong to the same phase. Alternatively, images in the same horizontal row have the same imst. 4) A green diamond on an upper left corner of a view port in which an image is displayed signifies that the image belongs to a current target phase, which is a target phase selected using the automatic image selection or is selected by the user from "Phase List-Select" region 150. 5) There exists vertical and horizontal scroll bars (not shown) to navigate through image viewer 154. 6) Window level, roam, zoom and paging operations are supported by the method. As an example, the user can page through all images in the same phase via a vertical paging icon (not shown) or can page through images with the same spatial location via a horizontal paging icon (not shown). 7) F-keys provided on the keyboard of console 40 to change a preset window level are supported by the method. The "Help" button provides access to on-line help documents.

Figure 10:
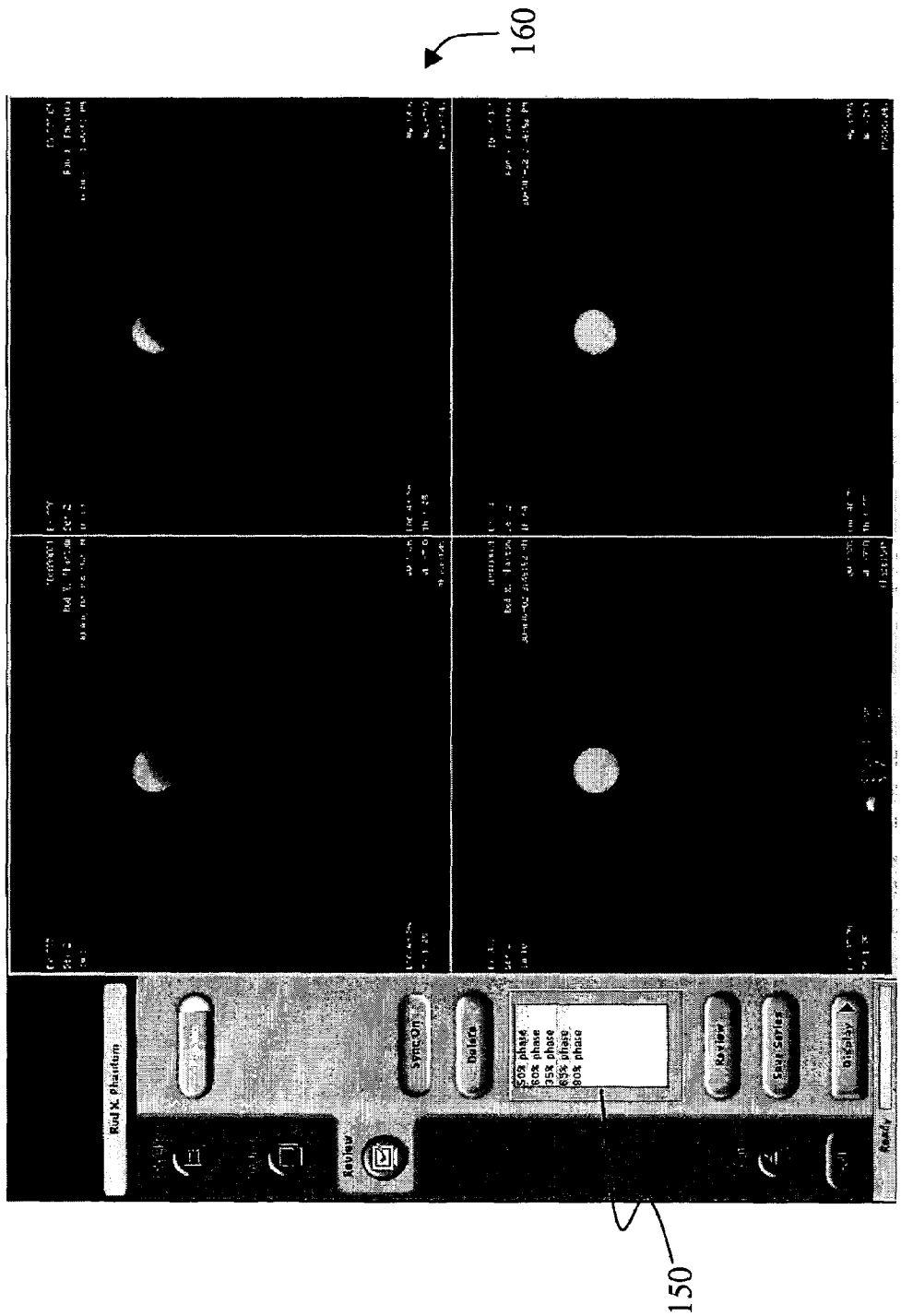
FIG. 10 shows an embodiment of an image review screen used by the user to review images that are selected by the user for each target phase.

FIG. 10 shows an embodiment of an image review screen used by the user to review images that are selected by the user for each target phase. The review of the images is optional. Image review screen includes an image viewer 160, a "Sync On" button, a "Delete" button, "Phase List-Select" region 150, a "Display" button, and the "Save Series" button.

The user can review images by selecting target phases in "Phase List-Select" region 150 and selecting a "Review" Button. Moreover, once an operation is requested, it is applied to all screens, including the image selection screen and the image review screen. For example, window level, roam, zoom and paging operations are similar to that on the image selection screen.

Different layouts can be used as a default format of image viewer 160 of the image review screen. As an example, a default format of image viewer 160 of image review screen is set to be a 2×2 layout. Arrangement of image viewer 160 depends on a number of phases the user has selected to review. As an example, if a single target phase is selected in "Phase List-Select" region 150, the default format is changed to a 1×1 layout where user can page through all images for a target phase. In the example, the user can use PageUp/PageDown keys (not shown) to page through the images. In the example, the user can switch the display format to 2×2 and use a PageUp/PageDown key to traverse through four images at a time. As another example, if two target phases are selected in "Phase List-Select" region 150, the display format available is the 2×2 layout. Left two viewports of image viewer 160 display images from a target phase that is selected first by the user, and the right two viewports display images from a target phase that is selected second by the user. The user can synchronize/de-synchronize paging of images via the use of the "Sync On" button. Image location is used to synchronize two image sets. In the 2×2 layout, the PageUp/PageDown key traverses through two images at a time. As yet another example, if three target phases are selected in "Phase List-Select" region 150, a 2×2 layout is available to review images from all three phases. In the example, the lower right viewport of image viewer 160 is empty. An upper left viewport of image viewer 160 displays images in a target phase selected by the user first, an upper right viewport of image viewer 160 displays images in a target phase selected by the user second, and a lower left viewport displays images in a target phase selected third by the user. The user can synchronize the review as mentioned above. In the example, a PageUp/PageDown key allows the user to traverse through one image at a time in all viewports of image viewer 160. As another example, if there are four or more target phases selected in "Phase List Select" region 150, the first four phases are displayed in a 2×2 layout. In the example, each viewport displays an image set for a target phase. In the example, the user can synchronize the review as mentioned above and a PageUp/PageDown key enables the user to traverse through one image at a time in all viewports of image viewer 160. F-keys to change preset window levels are supported by the method.

The "Sync On" button is used to synchronize or de-synchronize images in image viewer 160. The "Sync On" button toggles between synchronized and de-synchronized states.

The "Delete" Button is used to remove unwanted target phases. Functionality of the "Delete" button is similar to that described for the "Remove" button on the image selection screen.

"Phase List-Select" region 150 allows the user to select target phases to review. Multiple selection is available, however, only first four selected target phases are displayed on image viewer 160.

A display menu is accessed by selecting the "Display" button on the image review screen. The display menu includes at least one of the following options: 1) An image display format, for example, a 5×4 image display format, a 3×2 image display format, or a 2×1 image display format, where the 5×4 image display format is a default format. 2) An "Annotation On" of an "Annotation Off", where, for example, the "Annotation On" is a default. 3) A "Grid Line On" of a "Grid Line Off", where, for example, the "Grid Line On" is a default.

Once the user finishes reviewing images for each target phase, the user can save the images into storage device 38 via the "Save Series" button. The images are saved in a single phase-series fashion, where all images in the same target phase and the same phase tolerance are generated in the same series. The user can select a single target phase or multiple target phases from "Phase List-Select" region 150. When the "Save Series" Button is selected, a popup window is posted to display all existing phases in "Phase List-Select" region 150.

Figure 11:
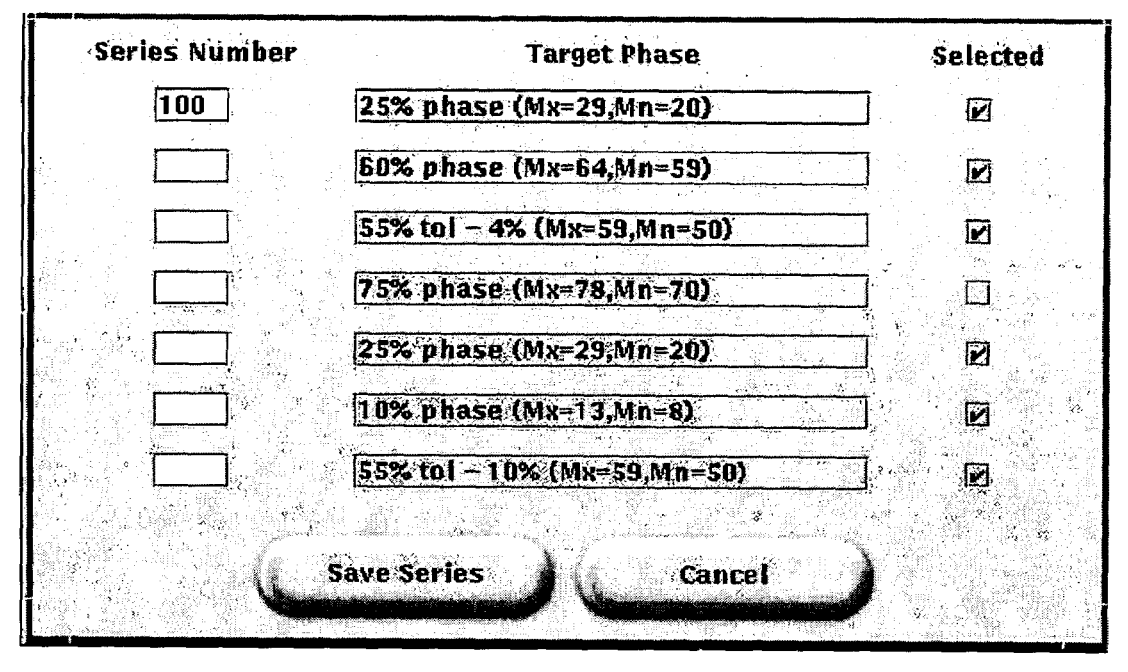

FIG. 11 shows an embodiment of a popup window that is displayed when the "Save Series" button is selected. Next to each field in which target phases of images are shown, there exists a series number text field to allow the user to enter the series number for each target phase to be saved. As an example, the series number is a positive number and has at most 3 digits. The user enters the Series Number of a target phase and has an option to leave remaining series number text fields empty. In such a case, the series number of the target phase entered to create series numbers for subsequent phases in an incremental fashion is used. For example, if the user designates "400" as a series number for phase 0, series numbers "410", "420" and so on for subsequent phases are created. In addition to the series number text fields, there exists a check box for each existing target phase. In one embodiment, the default is that check boxes corresponding to all target existing phases are checked.

On selecting the "Save Series" button, the method checks to ensure that a series number for a saved series does not currently exist in storage device 38. If duplication is detected, the user is notified of such duplicate series. The user has the option to change the series number or to proceed with the series number. When the user decides to proceed with the series number, images associated with target phases are generated and installed in storage device 38.

Series description for the saved series includes a target phase, a maximum phase, and a minimum phase. It is noted that in one embodiment, the target phase, the minimum phase, and the maximum phase are not saved in an image header of an image of a saved series.

It is also noted that the method for improving usability of images for medical applications can be implemented in a single photon emission computed tomography (SPECT) system, such as, a SPECT system that scans to provide 4D CT images. It is further noted that in an embodiment of the method, respiratory signal of patient 22 covers an entire scan. Otherwise, images having no corresponding respiratory signal ranges will not be considered during the automatic image selection. In such a case, a warning message is posted to inform the user of the error. Images, which do not have an associated respiratory signal are not displayed or selected by the automatic image selection. If the error of not having an associated respiratory signal is encountered after the automatic image selection, an image selected using the automatic image selection is clipped.

Moreover, it is noted that an embodiment of the method is executed in a cine full scan mode, where a scan duration at each z-location is equal to a sum of a respiratory cycle and speed of gantry, image slice thicknesses are 1.5 mm and 2.5 mm, coverage is 20-30 mm, a goal is to obtain 5 to 10 phases and 7 images at each spatial location, and a flat table top is provided for oncology applications. In another embodiment of the method, if one of H1, H2, H3, H4, and Pacific Star are used, a total number of images obtained is less than 1500, and if H16 or Hpower manufactured by General Electric Company are used, total number of images is less than 3000. Moreover, in the other embodiment, slice thickness, coverage and number of phases are selected by the user so that total number of images obtained do not exceed beyond 1500 for H1, H2, H3, H4, or Pacific Star and do not exceed beyond 3000 for H16 or Hpower. In yet another embodiment, PET/CT system 10 waits indefinitely for X-Ray source 14 to turn on after the user activates PET/CT system 10. In the embodiment, acquisition of respiratory signal stops if X-Ray source 14 turns off for 10 seconds.

Technical effects of the herein described methods and systems is to enable 2D viewing of axial images of each phase, to enable 3D volume rendering of each phase, to enable a physician to identify a respiratory cycle where an organ of interest has the largest clearance from surrounding organs to plan a treatment of patient 22, to stop respiratory motion so that anatomical information can be registered in the same spatial location over a long period of time for computation of a perfusion map, to enable use of a scalpel to isolate a tumor within patient 22, and to enable projection of the tumor at an arbitrary angle, and viewing of a 4D movie of images scanned using PET/CT system 10.

While the invention has been described in terms of various specific embodiments, those skilled in the art will recognize that the invention can be practiced with modification within the spirit and scope of the claims.

What is claimed is:

1. A method for retrospective internal gating, said method comprising:
    scanning a patient to obtain projection data;
    generating images from the projection data;
    obtaining a signal representing information regarding a physiological cycle of motion of an object within the patient;
    associating a plurality of sample points of the physiological cycle with each of the generated images, each plurality of sample points associated with phases of the physiological cycle;
    calculating a phase of each of the generated images based on an average of the phases of a respective plurality of sample points associated with each of the generated images;
    specifying at least one target phase in the physiological cycle of motion by calculating an average delta phase that is an average of phase differences between consecutive images of the generated images; and
    sorting the generated images based on the at least one target phase to generate at least one set of images.

2. A method in accordance with claim 1 further comprising receiving, from a user, a selection of a series of images from the at least one set of images, the selected series of images displaying a least amount of tissue motion compared to tissue motion of any other series in the at least one set of images.

3. A method in accordance with claim 1 wherein sorting the generated images based on the at least one target phase comprises:
grouping images having the same spatial location to generate at least one group, wherein each group includes images with a z-location different than a z-location of images within any other group; and
selecting one image in each group for inclusion within the at least one set of images.

4. A method in accordance with claim 3 wherein selecting one image in each group comprises selecting one image in each group, the image having a phase that lies within the at least one target phase and a phase tolerance.

5. A method in accordance with claim 3 wherein selecting one image in each group comprises selecting one image in each group, the image having a phase that lies within the at least one target phase and a phase tolerance, and is near a middle of an acquisition period of a scan of the patient.

6. A method in accordance with claim 1 further comprising:
validating the motion of the object by checking at least one of:
whether each cycle of a plurality of cycles of motion of the object is within a percentage of an average cycle of the plurality of cycles of motion of the object; and
whether an amplitude of each cycle of the plurality of cycles of motion of the object is within a percentage of an average amplitude of the plurality of cycles of motion of the object.

7. A method in accordance with claim 1 further comprising calculating phases of the images.

8. A method in accordance with claim 7 wherein calculating phases of the images comprises:
determining a start scan time, a mid scan time, and an end scan time for each of the generated images;
determining a mid scan sample point for each of the generated images;
determining, for each of the generated images, additional sample points symmetrically located around the mid scan sample point; and
computing a phase of each of the generated images by performing one of:
averaging phases of the mid scan sample point and of at least one of the additional sample points; and
averaging phases of at least one of the additional sample points.

9. A system for imaging a moving object within a patient, the system comprising:
a scanner configured to acquire projection data of the patient;
an image reconstructor configured to generate images corresponding to the projection data; and
a controller configured to:
receive a signal representing information regarding a cycle of motion of the object;
receive generated images from said image reconstructor;
associate a plurality of sample points of the cycle of motion with each of the generated images, each plurality of sample points associated with phases of the cycle of motion;
calculate a phase of each of the generated images based on an average of the phases of a respective plurality of sample points associated with each of the generated images;
enable a user to specify at least one target phase within the cycle of motion by calculating an average delta phase that is an average of phase differences between consecutive images of the generated images; and
sort the generated images based on the at least one target phase to generate at least one set of images.

10. A system in accordance with claim 9 wherein the controller is further configured to calculate phases of the images.

11. A system in accordance with claim 10 wherein to calculate phases of the images the controller is configured to:
determine a start scan time, a mid scan time, and an end scan time for each of the generated images;
determine a mid scan sample point for each of the generated images;
determine, for each of the generated images, additional sample points symmetrically located around the mid scan sample point; and
compute a phase of each of the generated images by performing one of:
averaging phases of the mid scan sample point and of at least one of the additional sample points; and
averaging phases of at least one of the additional sample points.

12. A system in accordance with claim 11 wherein the controller is further configured to determine a confidence level of each of the sample points by correlating image data acquisition times to acquisition times of each of the sample points.

13. A system in accordance with claim 11 wherein to determine additional sample points the controller is configured to determine if each of the additional sample points satisfies at least one of:
an X-Ray source of the scanner is turned on at a time corresponding to a respiratory sample point;
a confidence level for a respiratory sample point is non-negative;
a number of valid respiratory sample points used to calculate the phases of the images is defined via an environmental variable that is one of a minimum number of valid respiratory sample points and a maximum number of valid respiratory sample points;
the respiratory sample points of the cycle of motion are searched symmetrically from the mid scan sample point outward; and
a search for the valid respiratory sample points is limited to a total number of respiratory sample points falling within an acquisition period.

14. A system in accordance with claim 10 wherein to calculate phases of the images the controller is configured to specify a phase of a first image of the generated images as a first target phase.

15. A system in accordance with claim 14 wherein the controller is further configured to determine a subsequent target phase by adding the average delta phase to the first target phase.

16. A system in accordance with claim 10 wherein to calculate phases of the images the controller is configured to determine a number of phases by dividing $2\pi$ by the average delta phase.

17. A system for imaging a moving object within a patient, the system comprising:
a computed tomography (CT) scanner configured to acquire projection data of the patient;

an image reconstructor coupled to the CT scanner and configured to generate images corresponding to the projection data; and a controller coupled to the image reconstructor and configured to:
  receive a signal representing information regarding a cycle of motion of the object;
  receive generated images from said image reconstructor;
  associate a plurality of sample points of the cycle of motion with each of the generated images, each plurality of sample points associated with phases of the cycle of motion;
  calculate a phase of each of the generated images based on an average of the phases of a respective plurality of sample points associated with each of the generated images;
  enable a user to specify at least one target phase within the cycle of motion by calculating an average delta phase that is an average of phase differences between consecutive images of the generated images; and
  sort the generated images based on the at least one target phase to generate at least one set of images.

18. A computer configured to:
  instruct a scanner to acquire projection data of the patient;
  instruct an image reconstructor to generate images corresponding to the projection data;
  receive a signal representing information regarding a cycle of motion of the object;
  receive generated images from the image reconstructor;
  associate a plurality of sample points of the cycle of motion with each of the generated images, each plurality of sample points associated with phases of the cycle of motion;
  calculate a phase of each of the generated images based on an average of the phases of a respective plurality of sample points associated with each of the generated images;
  enable a user to specify at least one target phase within the cycle of motion by calculating an average delta phase that is an average of phase differences between consecutive images of the generated images; and
  sort the generated images based on the at least one target phase to generate at least one set of images.

19. A computer in accordance with claim 18 wherein the computer is further configured to receive, from a user, a selection of a series of images from the at least one set of images, the selected series of images displaying a least amount of tissue motion compared to tissue motion of any other series in the at least one set of images.

20. A computer-readable medium encoded with a program configured to:
  instruct a scanner to acquire projection data of the patient;
  instruct an image reconstructor to generate images corresponding to the projection data;
  receive a signal representing information regarding a cycle of motion of the object;
  receive generated images from the image reconstructor;
  associate a plurality of sample points of the cycle of motion with each of the generated images, each plurality of sample points associated with phases of the cycle of motion;
  calculate a phase of each of the generated images based on an average of the phases of a respective plurality of sample points associated with each of the generated images;
  enable a user to specify at least one target phase within the cycle of motion by calculating an average delta phase that is an average of phase differences between consecutive images of the generated images; and
  sort the generated images based on the at least one target phase to generate at least one set of images.

21. A computer-readable medium in accordance with claim 20 wherein the program is further configured to receive, from a user, a selection of a series of images from the at least one set of images, the selected series of images displaying a least amount of tissue motion compared to tissue motion of any other series in the at least one set of images.

* * * * *

UNITED STATES PATENT AND TRADEMARK OFFICE
CERTIFICATE OF CORRECTION

PATENT NO. : 7,620,444 B2  Page 1 of 1
APPLICATION NO. : 10/678839
DATED : November 17, 2009
INVENTOR(S) : Le et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 654 days.

Signed and Sealed this

Twenty-sixth Day of October, 2010

David J. Kappos
*Director of the United States Patent and Trademark Office*